US00PP35456P2

(12) United States Plant Patent
Hansen

(10) Patent No.: US PP35,456 P2
(45) Date of Patent: Nov. 7, 2023

(54) ***LEUCANTHEMUM* PLANT NAMED 'SEVENTH HEAVEN'**

(50) Latin Name: ***Leucanthemum* x *superbum* (Bergmans ex J.W.Ingram) D.H.Kent**
Varietal Denomination: Seventh Heaven

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 30 days.

(21) Appl. No.: 17/803,937

(22) Filed: Jan. 26, 2023

(51) Int. Cl.
*A01H 5/02* (2018.01)
*A01H 6/14* (2018.01)

(52) U.S. Cl.
USPC ..... Plt./285

(58) Field of Classification Search
USPC ..... Plt./285
CPC ... A01H 5/02; A01H 5/00; A01H 6/14; A01H 6/1424
See application file for complete search history.

(56) References Cited

U.S. PATENT DOCUMENTS

PP30,074 P2 * 1/2019 Hansen ..... A01H 5/02 Plt./285
PP33,851 P2 * 1/2022 Hansen ..... Plt./285

* cited by examiner

*Primary Examiner* — June Hwu

(57) ABSTRACT

The new Shasta daisy plant, *Leucanthemum* 'Seventh Heaven', is a sturdy plant with dark-green serrated foliage and stiff stems. The numerous, large, freely-flowering inflorescences producing two to three rows of overlapping horizontal ray florets beginning light-yellow and developing to creamy-yellow-colored. The center disk florets are golden yellow. The new plant is useful in the landscape as a long-flowering border, in mass, as accent plants and containerized for patio or indoor use, or as a cut flower.

1 Drawing Sheet

Botanical classification: *Leucanthemum* x *superbum* (Bergmans ex J.W.Ingram) D.H.Kent.

Variety denomination: 'Seventh Heaven'.

STATEMENT REGARDING PRIOR DISCLOSURES UNDER 37 CFR 1.77(B)(6)

The first non-enabling information of the claimed plant was made by Walters Gardens, Inc. on Feb. 1, 2022, in the form of a website brief description and photograph followed by a short description and photograph in the "Walters Gardens 2022-2023 Catalog" by Walters Gardens, Inc first distributed on Jun. 8, 2022. The first enabling disclosure of a sales of the claimed plant was on Jul. 7, 2022, by Walters Gardens, Inc. Walters Gardens, Inc. obtained the new plant and information about the new plant directly from the inventor. No plants of *Leucanthemum* 'Seventh Heaven' have been sold or offered for sale, in this country or anywhere in the world, nor has any disclosure of the new plant been made, more than one year prior to the filing date of this application, and such sale or disclosure within one year was either derived directly or indirectly from the inventor.

BACKGROUND OF THE INVENTION

The original *Leucanthemum* x *superbum*, or Shasta daisies, were bred by Luther Burbank in the late 1800's as a cross between *Leucanthemum maximum* (Ramond) DC. with *Leucanthemum vulgare* (Vaill.) Lam., *Leucanthemum lacustre* (Broth.) Samp. and *Nipponanthemum nipponicum*.

The new plant, *Leucanthemum* 'Seventh Heaven' originated from a planned breeding program of the inventor at a wholesale perennial nursery in Zeeland, Mich., USA. The new *Leucanthemum* was a single plant selected from a group of seedlings from a cross on Jun. 30, 2015, between the proprietary unreleased, unnamed proprietary hybrid known only by the breeder code 13-21-1 (not patented) as the female parent and 'La Crème' (not patented) as the male parent. The individual selected plant that eventually became 'Seventh Heaven' was first evaluated in the summer of 2017 and given the breeder number 15-127-1 through the subsequent evaluations.

The present invention relates to a new and distinct cultivar of Shasta daisy botanically known as *Leucanthemum* x *superbum* and hereinafter referred to by the cultivar name 'Seventh Heaven' or the new plant.

Asexual reproduction of the new cultivar by division at the same nursery in Zeeland, Mich. beginning in the summer of 2017 has demonstrated that the new cultivar reproduces true to type with all the characteristics of the original plant retained through successive generations of asexual propagation. The new plant has since been asexually propagated by basal shoot tip cuttings and sterile shoot tip tissue culture.

BRIEF SUMMARY OF THE INVENTION

The new plant, *Leucanthemum* 'Seventh Heaven', is most closely compared to: *Leucanthemum* 'Leumayel' U.S. Plant Pat. No. 19,242, 'Cream Puff' U.S. Plant Pat. No. 30,074, 'Banana Cream' U.S. Plant Pat. No. 23,181, 'Banana Cream II' U.S. Plant Pat. No. 33,851, 'Marshmallow' U.S. Plant Pat. No. 33,878, 'Goldfinch' U.S. Plant Pat. No. 24,499, and 'Real Goldcup' U.S. Plant Pat. No. 33,766.

'Leumayel' is slightly shorter in habit with less branching. In test trials in Zeeland, Mich., 'Cream Puff' has a shorter habit and has smaller inflorescences with ray florets that are less yellow. 'Banana Cream' has a taller and more upright habit, less branching, larger inflorescences, and thinner ray florets. 'Banana Cream II' has a taller, more upright, less mounded habit, and more inflorescences. 'Marshmallow' has a slightly taller habit and the inflorescences are more double with more laciniate and less yellowish ray floret ligules. 'Goldfinch' has a shorter upright habit, less branching, shorter and thinner ray florets that are initially bright lemon yellow and lighten to ivory white. 'Real Goldcup' has a much taller habit and shorter ray florets that are slightly more deeply emarginate.

The female parent has flatter, whiter and more ray florets. 'La Crème' has a more upright with less branching habit, and ray florets are smaller.

*Leucanthemum* 'Seventh Heaven' differs from all cultivars known to the inventor in the following combined traits:

1. Sturdy, dense, mounded plants with dark-green serrated foliage and stiff stems;
2. Large semi-double inflorescences with two or three rows of overlapping ray florets;
3. Ray florets with ligules starting light-yellow and becoming creamy-yellowish at maturity;
4. Center disk florets of golden yellow.

BRIEF DESCRIPTION OF THE PHOTOGRAPHS

The photographs of 'Seventh Heaven' demonstrate the overall appearance and landscape qualities of the new plant, including the unique traits planted in a full-sun trial garden in Zeeland, Mich. The colors are as accurate as reasonably possible with color reproductions. Ambient light spectrum, source, direction, and temperature may cause the appearance of minor variations in color.

DETAILED BOTANICAL DESCRIPTION

Figure 1:
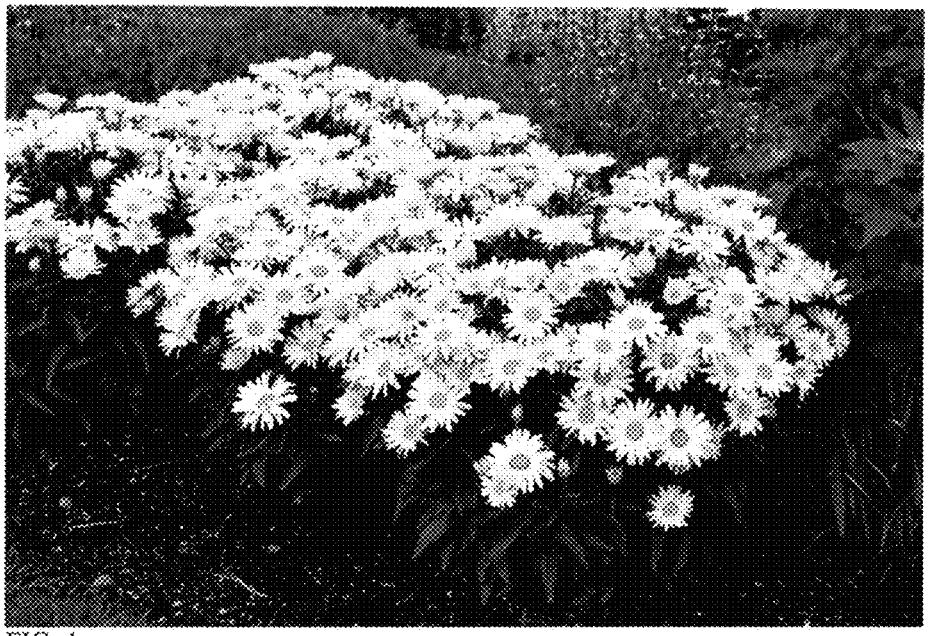
FIG. 1 shows a two-year-old new plant at peak flowering with inflorescences covering the plant from nearly top to ground.
Figure 2:
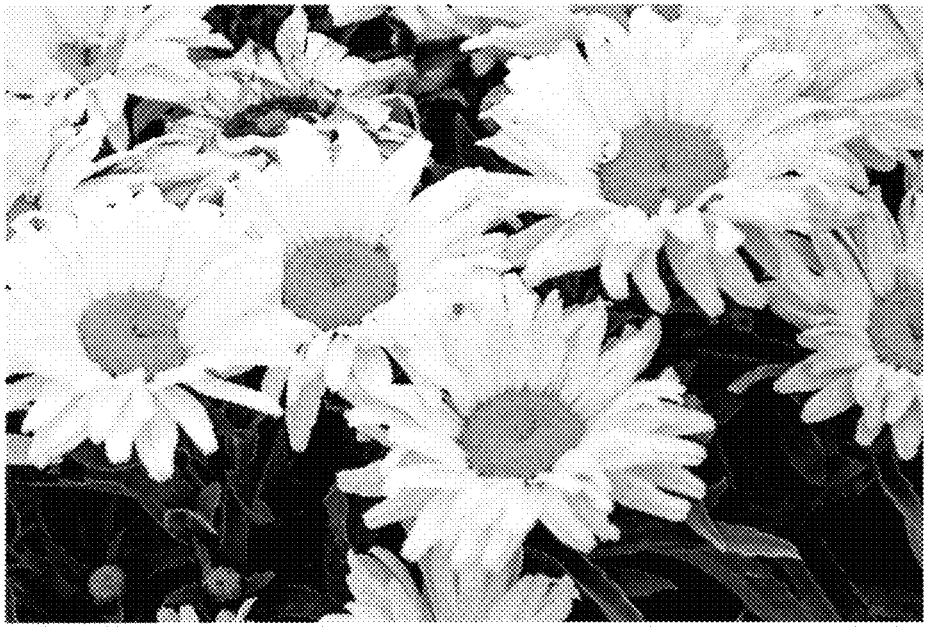
FIG. 2 shows a close-up of some inflorescences.

The following descriptions and color references are based on the 2015 edition of The Royal Horticultural Society Colour Chart except where common dictionary terms are used. The new plant has not been observed in all possible environments and conditions. The phenotype of *Leucanthemum* 'Seventh Heaven' may vary with different growing conditions such as changes in temperature, light intensity, water availability, and nutrition, but without change in the genotype.

The plants used for description purposes were three-year-old and were grown in Zeeland, Mich. in a full-sun, loamy-sand trial plot environment with supplemental water and limited fertilizer as needed and also a partially-shaded greenhouse. Summer temperatures range from night lows of about 10° C. to daytime highs of about 34° C. Measurements and numerical values represent averages or ranges of trial plants.

Botanical classification: *Leucanthemum* x *superbum;*

Parentage: Female parent is 13-21-1, male parent is 'La Crème';

Habit: Herbaceous perennial with about 30 to 40 branched stems arising from rhizome base; each stem having four to eight inflorescences each; about 49 cm to 56 cm tall and to about 93 cm across with rounded top;

Roots: Fibrous, thin, heavily branched; root color nearest RHS 155D depending on soil type;

Propagation: Tip cuttings or tissue culture; about two weeks to produce roots from cutting; about 33 weeks to finish to flower in a 3.8-liter pot depending on the season;

Stems: About 30 to 40 main stems per plant; strong; mostly upright; canaliculated; hispidulous; terete, hollow in distal portion; 9.0 mm diameter at base; to 52 cm tall; about 8 nodes before flowers; average internode length about 2.1 cm; with typically four to eight branches;

Stem color: Between RHS 146B and RHS 146A with ridges nearest RHS 146C;

Axillary branches: Four to eight; extending above main inflorescence; between 14 to 25 cm long and 2.5 to 4 mm diameter; upright to angles of about 30° or less from main stem;

Axillary branch color: Between RHS 146B and RHS 146A with ridges nearest RHS 146C;

Leaves: Lanceolate to linear; apex acute; proximal leaf bases petiolate and attenuate, with cauline leaf bases sessile, truncate to clasping; alternate; sparsely puberulent adaxial and abaxial; margin serrate and micro-ciliolate with average about eleven teeth per side, and size average about 1.5 mm long and 1.5 mm wide; proximal leaves to about 14.2 cm long and 4 cm wide, lower cauline leaves to about 15 cm long, 4.5 cm wide near middle; average about 9.3 cm long and 3.5 cm wide; no fragrance detected;

Leaf color: Young adaxial between RHS 137A and RHS 137B distally and nearest RHS 138A proximally, abaxial nearest RHS 137B distally and RHS 138A proximally; mature adaxial between RHS 137A and RHS 139A, abaxial nearest RHS 147B;

Petiole: On basal leaves only, not on cauline leaves; concavo-convex; micro-puberulent and slightly lustrous adaxial and abaxial, to 9 cm long and 11 mm across at base;

Petiole color: Adaxial midrib nearest RHS 145D with surrounding portion nearest RHS 145B and margin nearest RHS 146B; abaxial midrib nearest RHS 145B with surrounding portion nearest RHS 146D and margin nearest RHS 146B; adaxial and abaxial basal 20 mm nearest RHS 145D strongly maculate with nearest RHS 187C;

Veins: Anastomosing; glabrescent adaxial and pubescent to puberulent abaxial; adaxial slightly raised, abaxial midrib costate and secondary veins smooth;

Vein color: Adaxial midrib nearest RHS 145D proximally and distally midrib and secondary veins nearest RHS 137B; abaxial midrib nearest RHS 146D proximally and distally nearest RHS secondary veins nearest RHS 147B;

Inflorescence: Capitate; about 150 per plant at one time; primary inflorescence 10 cm across and 3.5 cm tall; comprising two or three outer rows of imbricate ray florets and about 175 to 300 central disk florets; individual inflorescence lasting about three weeks on or cut from plant; upright;

Fragrance: Faint dirty fragrance detected;

Flowering period: Early July to early August in Michigan;

Peduncle: Strong, stiff; hispidulous to puberulent; cylindrical; striate with ridges; 6 cm to 50 cm long and about 9 mm diameter at base; erect attitude;

Peduncle color: Between RHS 146B and RHS 146A with ridges nearest RHS 146C;

Bud: With ray florets still vertical — oblong globose; 4 cm across ray florets and 3 cm from base of phyllaries to apex of capitulum;

Bud color: Adaxial and abaxial ray floret ligule nearest RHS 8D distally, central portion between RHS 10B and RHS 10C adaxial and between RHS 13C and RHS 13D abaxial, base nearest RHS 146D; phyllaries nearest RHS 138A in center and margin nearest RHS 196D;

Floret type: Ray florets on the exterior two rows, disk florets in inflorescence center;

Ray florets: To about 44 per inflorescence; pistillate; arranged around outer perimeter of capitulum in two overlapping rows; ligules glabrous adaxial and abaxial, base attenuate rolled into claw, apex emarginate with typically two notches indented to about 0.5 mm, margin entire; to about 52 mm long and 9 mm wide; flat to reflex in distal 10 mm;

Disk florets: Perfect; incomplete; tubular; to about 175 to 300 per inflorescence at center of capitulum; combined inflorescences disk to about 26 mm across and about 12 mm tall; individual floret about 10 mm tall and 2 mm wide; five tepals, about 6 mm long; with acute apex, fused in basal 5 mm;

Ray floret color: When ray floret ligules are first horizontal adaxial nearest RHS 9D in middle portion, apex nearest RHS 13C, base between RHS 146D and RHS 144A, abaxial middle portion nearest RHS 4D, apex nearest RHS 6C, and base nearest RHS 146C; mature adaxial and abaxial ligules nearer RHS 155B than RHS 4D with the basal 9 mm portion nearest RHS 143C; before dropping adaxial middle portion between RHS 13D and RHS 155A, apex nearest RHS 155A, base nearest RHS 146C, abaxial middle portion nearest RHS NN155A, apex nearest RHS 155B and base nearest RHS 146C;

Disk floret color: Young adaxial and abaxial corolla tube nearest RHS 13B in distal 1 mm, next distal 2 mm translucent with veins nearest RHS 146D, corolla tube base nearest RHS 148B; mature adaxial and abaxial corolla tube nearest RHS 13B distally, center transparent and base nearest RHS 148B;

Androecium: Five stamens connate around style;

*Anther*.—Five; connate into tube; about 3 mm long and less than one mm wide, not present in ray florets, functional in disk florets; color nearest RHS 17B.

*Filaments*.—Fused together at apex, 3 mm long and less than 0.1 mm diameter; color translucent to between RHS 146D and RHS 145D.

*Pollen*.—Only found in disk florets; color nearest RHS 21A.

Gynoecium: In ray florets and disk florets; to about 10 mm long; exserted;

*Style*.—About 7 mm long and less than 0.3 mm diameter, bifid and reflex in apical 1 mm; color between RHS 146D and RHS 145D.

*Stigma*.—Bifid; to about 1.5 mm long and less than 0.5 mm diameter; color nearest RHS 145D.

Involucre: Made of about two layers of phyllaries; to 3 cm across and 0.9 cm tall;

Phyllaries: Lanceolate; apex acute; base truncate; imbricate; adaxial and abaxial glabrous, matte; margin micro-erose and translucent; to about 9 mm long and 3 mm wide;

Phyllaries color: Adaxial and abaxial outer 1.0 mm of margin transparent; adaxial nearest RHS 146D with a midrib nearest RHS 138A, abaxial nearest RHS 138A, adaxial and abaxial apex nearest RHS 200A;

Fruit: Achene, pointed at base and rounded at distal end with longitudinal color striations nearest RHS N200A and lighter than RHS 155D; about 3 to 4 mm long and 1.5 mm across;

*Leucanthemum* 'Seventh Heaven' grows best with adequate moisture but can tolerate some dryness once established. Vernalization is not required for flowering but is beneficial. The new plant is tolerant of high temperatures of at least 36° and cold hardy to at least USDA zone 5 as well as strong wind and rain. Other disease or pest resistance beyond that common to Shasta daisy has not been observed.

I claim:

1. The new and distinct Shasta daisy *Leucanthemum* plant named 'Seventh Heaven' as herein described and illustrated.

* * * * *